US005721142A

United States Patent [19]

Klemm et al.

[11] Patent Number: 5,721,142
[45] Date of Patent: Feb. 24, 1998

[54] METHOD FOR MONITORING MAMMALIAN REPRODUCTIVE CYCLES

[75] Inventors: William Robert Klemm, Bryan, Tex.; Germain Francois Rivard, Philadelphia, Pa.

[73] Assignee: Texas A & M University System, College Station, Tex.

[21] Appl. No.: 293,666

[22] Filed: Aug. 22, 1994

[51] Int. Cl.⁶ ............................ A61B 10/00; G01N 33/48
[52] U.S. Cl. ........................ 436/65; 436/128; 436/161; 436/181; 436/900; 436/906; 128/738
[58] Field of Search ..................... 436/63, 65, 128, 436/161, 174, 181, 900, 906; 128/738

[56] References Cited

U.S. PATENT DOCUMENTS

| 3,436,186 | 4/1969 | McSweeney et al. | 436/65 |
|---|---|---|---|
| 3,986,494 | 10/1976 | Preti et al. | 128/738 |
| 4,010,738 | 3/1977 | Preti et a. | 128/738 |
| 4,036,212 | 7/1977 | Karuhn | 436/65 X |
| 4,119,089 | 10/1978 | Preti et al. | 436/65 |
| 4,358,288 | 11/1982 | Goldman | 436/65 |
| 4,385,125 | 5/1983 | Preti et al. | 436/65 |
| 4,390,633 | 6/1983 | Merilan et al. | 436/65 |
| 4,467,814 | 8/1984 | Preti | 128/738 |
| 4,931,403 | 6/1990 | Cutler et al. | 436/65 |

FOREIGN PATENT DOCUMENTS 2251432  11/1991  United Kingdom .

OTHER PUBLICATIONS

Volatile constituents of human vaginal secretions, G. R. Huggins, M.D. et al., American Journal of Obstetrics and Gynecology, vol. 126, No. 1, pp. 129–136 (Sep. 1, 1976).

Acetaldehyde As a Possible Marker & Predictor of Bovine Estrus, W. R. Klemm, Texas A & M University, 8 pages, Beef Cattle Research in Texas, 1992; Jul., 1993.

Blood acetaldehyde fluctuates markedly during bovine estrous cycle, W. R. Klemm, G. F. Rivard, B. A. Clement, Animal Reproduction Science, 35:9–26 (1994).

Gas Chromatographic Analysis and Estrous Diagnostic Potential of Headspace Sampling Above Bovine Body Fluids, G. F. Rivard and W. R. Klemm, Chemical Signals in Vertebrates VI, 115–118, Plenum Press, New York, 1992.

Primary Examiner—Long V. Le
Attorney, Agent, or Firm—Vaden, Eickenroht & Thompson, L.L.P.

[57] ABSTRACT

A method for monitoring mammalian reproductive cycles by monitoring variations in the quantity of one or more low molecular weight volatile compound having a molecular weight of less than 50 grams per mole present in a body constituent sample is disclosed. Samples of a body constituent selected from the group of humoral fluid, breath and body cavity air are collected from a female mammal a multiple number of times during the reproductive cycle. The quantity of a low molecular weight volatile compound in each sample is measured. In the preferred embodiment, the low molecular weight volatile compound, acetaldehyde, will be measured and monitored. Variations in the quantity of the low molecular weight volatile compound appearing in each sample is monitored to determine the phase of the mammal's reproductive cycle and to predict the occurrence of ovulation.

35 Claims, No Drawings

5,721,142

METHOD FOR MONITORING MAMMALIAN REPRODUCTIVE CYCLES

ORIGIN OF THE INVENTION

The invention described herein was made using federal funds and the United States Department of Agriculture shall have the non-exclusive right to practice the invention for government purposes on behalf of the United States throughout the world.

FIELD OF THE INVENTION

The invention relates to monitoring variations in the quantity of low molecular weight volatile compounds present in body constituents of mammals to determine phases of the reproductive cycle and to predict the occurrence of ovulation. The invention also relates to monitoring variations in the quantity of low molecular weight volatile compounds present in body constituents of animals to detect the onset of estrus and predict the occurrence of ovulation.

BACKGROUND OF THE INVENTION

Monitoring reproductive cycles and predicting the time of ovulation in mammals is of great importance to human reproduction and the production of livestock and other animals. Means currently available for detecting ovulation, however, have considerable limitations. For example, surgical techniques for detecting ovulation require that incisions be made so the corpus luteum of the ovary can be observed for physical signs of ovulation. Such a procedure is undesirable and has not gained widespread acceptance. Moreover, clinical evaluations, such as monitoring pelvic discomfort or monitoring basal body temperature are not widely accepted because of the imprecision of the methods and their unreliability for predicting ovulation.

Various biochemical and histological methods for detecting ovulation are also available. Cyclic variations in the concentrations of certain hormones appearing in the blood, such as rises in serum estrogen with a rise in luteinizing hormone, are known indicators of impending ovulation in humans. Measuring the glucose concentration in cervical mucosa and measuring salivary alkaline phosphatase levels have also been explored as methods for detecting ovulation. Because of the risk of sample contamination and the amount of technical expertise required to accurately perform necessary collections and analyses, histological and biochemical tests for predicting the occurrence of ovulation often require trained personnel to perform the procedures. Many of these methods, however, remain unreliable in predicting the onset of the fertile period or the occurrence of ovulation.

Vaginal secretions have been monitored for the concentration of volatile organic compounds having a molecular weight between 50 and 350 grams per mole for use as predictors of the fertile period and ovulation. U.S. Pat. No. 3,986,494, "Method of Predicting and Detecting Ovulation", Preti et al., Oct. 19, 1976. The concentration of a particular volatile organic compound, such as acetic or lactic acid, is used to diagnose the occurrence of ovulation in the menstrual cycle. The compounds monitored have a first increase in concentration just prior to the rise in serum estrogens, thereby indicating the onset of the fertile period. At least four days after the first increase, a second increase in the volatile organic compound indicates the time of ovulation. This method is estimated to be useful in accurately predicting the fertile period and ovulation in approximately only 80% of the female human population.

U.S. Pat. No. 4,010,738, "Method of Predicting and Detecting Ovulation", Preti et al., Mar. 8, 1977, discloses monitoring urea concentrations in vaginal secretions of mammals as a method of diagnosing the onset of the fertile period or ovulation. As with other methods known for monitoring various compounds in vaginal secretions, the likelihood of contamination of the secretion with other body secretions or feces is great. Moreover, urea concentration is influenced by nutrition and digestion, and is not a reliable indicator of reproductive cycle events.

Other methods for detecting the onset of the fertile period and ovulation include monitoring the volatile sulfur content of mouth air. U.S. Pat. No. 4,119,089, "Method of Predicting and Determining Ovulation by Monitoring the Concentration of Volatile Sulfur-Containing Compounds Present in Mouth Air", Preti et al., Oct. 10, 1978. The volatile sulfur content of mouth air is believed to be a secondary characteristic which is responsive to elevated levels of female sex hormones. A first marked increase in the concentration of volatile sulfur compounds after menses is reported as being predictive of ovulation. A second marked increase in sulfur concentration is reported to be diagnostic of ovulation. Although detection of volatile sulfur content of mouth air may in some way be correlated to, or at least occurring at similar times with particular periodontal conditions occurring at ovulation, the volatile sulfur content of mouth air may also be influenced by other systemic conditions. Thus, it may not be a reliable predictor of ovulation.

Methods for determining the occurrence of estrus in cattle have also been disclosed. Direct rectal palpation or ultrasonography of the ovaries can be performed, however, it is not a viable choice for use in the field by farmers and dairymen. Similarly, measuring the pulsatile release of luteinizing hormone (LH) in serum is not a practical means for monitoring estrus by livestock producers. Other means for detecting estrus, such as serum or milk progesterone level measurement and electronic conductivity tests of cervicovaginal mucus are not accurate and give only retrospective evaluation of the reproductive cycle.

Cow vaginal secretions may be collected over time to determine a significant increase in the amounts of an indicator compound in the secretions. U.S. Pat. No. 4,467,814, "Method for Detecting Bovine Estrus by Determining Methyl Heptanol Concentrations in Vaginal Secretions", Preti et al., Aug. 28, 1984. The indicator compounds are eight-carbon alcohols such as methyl-1-heptanols, particularly 6-methyl-1-heptanol. Specific quantities of the indicator compounds are reported as indicative of estrus. The high risk of contamination and the requirement that specific quantities of compound be identified, as opposed to monitoring variations in quantities, in order to predict estrus make such a method undesirable for monitoring estrus cycles.

Volatile compounds present in blood have been investigated for use as indicators of estrus. Klemm et al., Blood acetaldehyde fluctuates markedly during bovine estrous cycle, In press, *Anim. Reprod. Sci.*; Klemm, W. R., Acetaldehyde As a Possible Marker and Predictor of Bovine Estrus, In press, *Beef Cattle Research in Texas*. The low molecular weight compound acetaldehyde was found to increase a few days before behavioral signs of estrus and decrease markedly on the day of estrus or shortly thereafter. Methods for measuring and monitoring acetaldehyde levels in blood or other humoral fluids would allow estrus and/or ovulation in mammals to be predicted.

There remains a great need for a simple, universally acceptable method for detecting and diagnosing mammalian reproductive cycle phases, particularly the occurrence of ovulation. While the shortcomings of the methods discussed apply for mammalian species; predicting ovulation in human females is even more difficult because there are not clear behavioral signs that ovulation is about to occur.

Accurately identifying the time of ovulation in mammals will dramatically increase the likelihood that fertilization occurs and offspring is produced. In cases of particular human medical concerns, such as infertility, diagnosing the time of ovulation is critical to conception. Accurately predicting ovulation will also enable developing reliable rhythm-type birth control methods for humans.

Predicting the occurrence of estrus and ovulation is economically important to livestock breeders, particularly cattle breeders. In order to increase milk production in dairy cattle, and maximize offspring in both dairy and beef cattle, detection of estrus is required. Detecting and predicting estrus and ovulation is particularly important in dairy herds, where artificial insemination is nearly exclusively used to produce fertilization. Larger dairy herd sizes and rising labor costs further increase the need for a method for easily and accurately detecting estrus. Because bovine estrus (lordosis or standing mating behavior) is short (1–18 hours, mean 4.4 hours), with ovulation occurring at about 12 hours after the onset of estrus, there is a herd management need to develop simple chemical tests for compounds that could serve as biochemical markers and predictors of estrus and ovulation. Identification of one or more compounds in a readily accessible body constituent would be an important step in detecting bovine estrus. The common practice of visual monitoring and measuring blood progesterone as indexes of stage of estrus could then be replaced by a more accurate method for detecting estrus and ovulation.

SUMMARY OF THE INVENTION

The present invention is a method for monitoring mammalian reproductive cycles by monitoring variations in the quantity of one or more low molecular weight volatile compound subject to variation during the reproductive cycle present in a body constituent sample. Samples of a body constituent selected from the group consisting essentially of humoral fluid, breath and body cavity air, are collected from a female mammal a multiple number of times during the reproductive cycle. Humoral fluid samples can be selected from the group consisting essentially of blood, vaginal secretions, saliva, urine, milk, sweat, skin gland secretions, follicular fluid, and the air above a humoral fluid. The quantity of a low molecular weight volatile compound in the sample is measured by using head-space gas chromatography, a chemical reagent test, electrochemical detector, or other technique known for measuring the quantity of the low molecular weight volatile compound present. The low molecular weight volatile compound will have a molecular weight of less than 50 grams per mole. In the preferred embodiment, the low molecular weight volatile compound, acetaldehyde, will be measured and monitored. Variations in the quantity of the low molecular weight volatile compound appearing in each sample is monitored to determine the phase of the mammal's reproductive cycle and to predict the occurrence of ovulation.

The body constituent sample may be separated into a nonvolatile compounds fraction and a volatile compounds fraction whereby the volatile compound's fraction of the sample collected is analyzed. Breath and body cavity air samples may be collected from within the mouth or body cavity, respectively, or from the outside of the mammal's body.

The body constituent samples may be taken from primates or non-primates. Variations in the quantity of low molecular weight volatile compound are monitored in primates to predict the occurrence of ovulation, wherein the low molecular weight volatile compound in the body constituent sharply increases over baseline levels prior to ovulation and then decreases to approximately baseline levels near or at the time of ovulation. The quantity of low molecular weight volatile compound in the sample of the body constituent of non-primates sharply increases over baseline levels before estrus and decreases at approximately estrus. Monitoring the variations in the quantity of low molecular weight volatile compounds present in body constituent samples in nonprimates will enable predicting the occurrence of ovulation and/or estrus.

Predicting estrus and ovulation in animals can be accomplished by monitoring variations in the quantity of one or more low molecular weight volatile compound subject to variation during the reproductive cycle in a body constituent selected from the group consisting essentially of humoral fluid, breath and body cavity air. Humoral fluid can be selected from the group consisting of blood, vaginal secretions, saliva, urine, milk, sweat, vulval, skin gland secretions, follicular fluid and the air above a humoral fluid. The low molecular weight compound measured in the body constituent samples will have a molecular weight of less than 50 grams per mole. In the preferred embodiment, the low molecular weight volatile compound, acetaldehyde, is measured and variations monitored. The samples are collected a preselected number of times during proestrus and the quantity of low molecular weight volatile compound in each sample measured. Monitoring variations in the quantity of the low molecular weight volatile compound can be used to predict the onset of estrus and ovulation. The quantity of low molecular weight volatile compound appearing in the body constituent sample will sharply increase over baseline levels shortly before estrus and decrease at approximately the onset of estrus whereby the occurrence of ovulation can then be predicted.

Samples of breath or body cavity air may be taken from the mouth or the body cavity, respectively, or from outside the animal's body. The quantity of low molecular weight volatile compound in a body constituent sample may be measured using head-space gas chromatography, a biochemical reagent test or other technique known for measuring the quantity of the low molecular weight volatile compound present.

The occurrence of ovulation in animals in the field may be predicted by monitoring variations in the quantity of the low molecular weight volatile compound in a body constituent during the reproductive cycle. The quantity of low molecular weight compound in the body constituent may be measured using a chemical reagent test. A kit is provided comprising an air adsorption tube containing an adsorbent with which the low molecular weight volatile compound reacts. A pump having a flow control meter will draw a body constituent sample through the air adsorption tube at a calibrated rate so as to expose the air to the adsorbent, thereby trapping the low molecular weight volatile compound. In the preferred embodiment, 1-(hydroxymethyl) piperidine is the adsorbent. In an alternate embodiment, di-nitrophenyl hydrazine may be used as the adsorbent. In yet another embodiment, 1,3-cyclohexanedione may be used as the adsorbent. The quantity of the low molecular weight volatile compound is measured using ultraviolet spectroscopy techniques.

The quantity of low molecular weight compound in the body constituent may also be measured using a kit comprising an electrochemical detector and means for signalling a change in the quantity of the low molecular weight volatile compound.

DETAILED DESCRIPTION

Body constituents, such as humoral fluids, breath and body cavity air, may be collected multiple times over a predetermined period of time from mammals and analyzed to measure the quantity of a low molecular weight volatile compound or compounds subject to variation during the reproductive cycle present in the body constituent. Variations in the quantity of low molecular weight volatile compound measured is used for monitoring the mammal's reproductive cycles and to predict ovulation. Humoral fluids include blood, vaginal secretions, saliva, urine, milk, sweat, skin gland secretions, follicular fluid and the air above the humoral fluid. For example, the air above or adjacent to a milk sample or milk in bulk, can be analyzed to measure the quantity of low molecular weight volatile compound present. Body cavity air may be sampled from the lungs and reproductive tract, as well as other body cavities.

The body constituents can be used as a source of one or more low molecular weight volatile compounds, which provides a chemical signal for determining and predicting the occurrence of ovulation and other reproductive cycle events in mammals. Although one or more body substance may be sampled and analyzed for one or more low molecular weight compounds to monitor mammalian reproductive cycles, for purposes of this discussion both body constituent and low molecular weight compound will be discussed in the singular form.

In the preferred embodiment of the present invention, body constituent samples are collected from a selected mammal or group of mammals multiple times during a reproductive cycle. Samples of humoral fluids, breath and body cavity air may be taken directly, using sampling protocols known to those skilled in the art. The samples are then analyzed to monitor variations in the quantity of low molecular weight compound present. Variations in the quantity of low molecular weight compound can be used to monitor and predict the occurrence of ovulation and/or estrus. In the alternative, the air emitting from the body cavity of a mammal, such as the air external to a mammal's vagina or reproductive cavity at the vulva, may be sampled. As another alternative, samples of the air above a humoral fluid can be collected for analysis.

The body constituent samples are analyzed to measure the quantity of the low molecular weight volatile compound in the sample. Low molecular weight volatile compound is used herein to refer to small, volatile organic compounds having a molecular weight of less than 50 grams per mole. The quantity of a low molecular weight volatile compound may be expressed as concentration, parts per million (ppm), or other standard quantitative expression, depending upon the body constituent sampled and the analytical procedures used to measure the quantity of the compound. Monitoring the variations in the quantity of the low molecular weight compound present in a sample can be used to determine and predict phases of the reproductive cycle, such as the occurrence of ovulation. A sharp and sudden increase in the quantity of the low molecular weight volatile compound followed by a sharp and sudden decrease in the quantity of the low molecular weight volatile compound in the body constituent sample indicates that the mammal is at or near ovulation and/or estrus. Body constituents of mammals will contain a baseline (generally lower) quantity of low molecular weight compounds subject to variation during the reproductive cycle during the other phases of the cycle.

Body constituent samples may be analyzed using head-space gas chromatography, chemical reagent tests, or electrochemical detectors, as well as other analytical tools such as biochemical, immunochemical and photochemical methods for measuring the quantity of low molecular weight volatile compound. In the preferred embodiment, body constituent samples are analyzed using head-space gas chromatography following the protocol described in Example I.

EXAMPLE I

Whole blood samples were collected during 18 estrous cycles from five group-housed adult female cattle. The cattle were fed and watered ad libitum, and observed daily between 08:00 and 10:00 h for signs of standing heat behavior (mounting and standing for being mounted). If needed, cows were also observed in late afternoons near the expected time of estrus. Some of the cycles were induced by hormone treatment consisting of two daily injections of follicle stimulating hormone (FSH) followed by an injection of prostaglandin F2$\propto$ (PG) two days later. A total of 164 samples were analyzed according to the following head-space gas chromatography protocol to measure the quantity of the low molecular weight volatile compound, acetaldehyde, having a molecular weight of approximately 44 grams per mole. The blood samples were collected in early morning by venipuncture.

The samples were prepared by placing a 10 ml aliquot of blood with 10% sodium citrate in a 30 ml injection vial, which was sealed with a teflon-coated septum. The samples were rapidly frozen and stored at $-80°$ C. until being prepared for analysis by gas chromatography. For analysis, the samples were thawed and warmed to 40° C., a temperature similar to that of the body temperature of the animal. It is preferred that the samples be handled at a temperature that does not exceed the body temperature of the mammal.

Upon thawing of the samples, the air (vapor phase) above the whole blood will contain the volatile compounds. The vapor phase provides a natural process for separating the volatile compounds fraction from the nonvolatile compounds fraction of the blood. Head-space gas is withdrawn with an air-tight syringe that has been heated to prevent carry-over of volatile compound which would otherwise condense or adsorb on the glassware. The injection of air must be small enough to achieve an injection that is rapid enough to produce clearly resolved peaks. In the preferred method, approximately 1 ml of air injected achieved a rapid injection suitable for analyzing the volatile compounds.

The chromatographic temperature profile began at room temperature in order to get retention and separation of the lower molecular weight, more volatile compounds. The blood head space was injected into the splitless port of a Hewlett Packard HP-5890 gas chromatograph. A 10 m fused silica pre-column, in series with a 15 m HP-5 (Hewlett Packard) (0.53 mm I.D., film thickness 2.65 µm) and a 15 m BP-1 (SGE) (0.53 mm I.D., film thickness 5.0 µm) nonpolar columns were used. As an alternative, a 30 m DB-1 nonpolar column (J & W Scientific, Folsom, Calif.) may be used.

Column temperature began at 30° C. and was held at that temperature for 10 minutes, followed by an increase of 4° C. every minute until a temperature of 110° was reached. The injector temperature was 180° C. and flame ionization detector (FID) temperature was 200° C. The flow rate of the helium carrier gas was 4.1 ml min$^{-1}$. Peak areas were calculated with the PC software "ChromPerfect" by Justice Innovations, Inc., Palo Alto, Calif.

Acetaldehyde was eluted in the first few minutes at room temperature as the third peak. The typical chromatographic profile revealed an initial double peak followed by two clearly distinguishable peaks. The peaks shown all eluted within 4 minutes (when the column was still at room temperature). Day 0 is the day when the cow stood for mounting, which is the typical behavioral sign of bovine estrus. Day 0 was confirmed by rectal palpations of the ovaries. Acetaldehyde increase on days −3 (3 days before standing estrus) to −1 (one day before standing estrus).

In the first three cows studied in the spring and summer through four cycles each, acetaldehyde increased several days before estrus and then decreased. The changes in acetaldehyde in blood head space ($nmol^{-1}$) during four estrous cycles in three cows were observed. In all cycles, the relative amounts of acetaldehyde increased and then suddenly decreased at or near estrus. The size of the peak representing acetaldehyde varied widely during the cycle and among cows. However, all cows typically showed a similar qualitative pattern of a rise and then fall in peak area at or near the time of estrus (the day when cows will stand still for mounting).

A "baseline" quantity of acetaldehyde appearing in samples was found, although the quantity varied from animal to animal. "N" signifies that the estrus was natural (not preceded by FSH and PG injections). Absolute values were calculated from aqueous solutions of authentic standards of acetaldehyde. Acetaldehyde (peak 3) was also found to be correlated with the sexual hormones estrogen and progesterone. It was discovered that acetaldehyde increased the day or so before estrogen rise until the day (+/−1) of standing estrus, whereupon acetaldehyde decreased to low or undetectable levels.

Similarly, the changes of acetaldehyde in blood head space during six estrous cycles in two other cows were observed. The relative amounts of acetaldehyde again increased and then decreased at or near estrus in all six cycles. The first estrus in both cows was triggered by injection of FSH and PG. Similar results were observed for both hormone-induced and natural ("N") estrus.

In all five cows the absolute amounts of acetaldehyde varied greatly from cow to cow, but the qualitative patterns during estrous cycles were similar. Near the time of estrus, there was a sudden rise and then a sharp fall of blood acetaldehyde just prior to standing estrus.

Acetaldehyde was confirmed as the low molecular weight volatile compound by preliminary mass spectral analysis. The blood samples were spiked with candidate compounds to determine which compound co-eluted with the peak of interest. To collect sufficient quantity of the compound for mass spectral identification, 10 ml aliquots of blood were subjected to the following procedures in order to determine whether the yield of acetaldehyde in the head space could be increased:

1. Shaking the samples at 50° C. for 3 min with a Mistral Multi-mixer.

2. Heating samples to various temperatures, starting at 30° C. and increasing by 10° C. up to 100° C.

3. Leaving samples in a 90° C. water bath for varying lengths of time, starting with 10 min and increasing by 10 min up to 60 min.

4. Samples with varied sample phase fraction (SPF), which refers to the ratio of liquid to head-space volume in the sealed injection vial, was varied from 33% to 40%, and from there, in 10% increments to 90% SPF.

5. Samples had nanopure water added to their sealed vials, starting with 2.5 ml and increasing by 2.5 ml up to 10 ml. The extra pressure accumulated in the vials was not vented. The effect of reducing water content of the sample by adding a molecular sieve compound (60/80 mesh, Supelco, Bellefonte, Pa.) was also tested. After sealing a vial containing the 0–4 g of sieve, 10 ml of air was withdrawn nd the 10 ml of blood injected. Samples were frozen and later tested under the standard conditions of standing for 30 minutes at 90° C.

6. Samples has 1–4 g sodium chloride added, and were compared to samples having 1–8 g potassium carbonate added. The salts were added to frozen blood, which was sealed in the serum vial and then allowed to thaw.

Shaking the samples had no effect on the quantity of acetaldehyde in the head space. Heating samples to various temperatures, starting at 30° C. and increasing by 10° C. up to 100° C. produced approximately a ten-fold increase in acetaldehyde quantity. Temperature effects on quantity of blood head-space compounds were observed. Equilibrating samples in the water bath produced only about a two-fold increase in acetaldehyde. Increasing the percentage of total SPF in the sealed vial between 33% and 90% caused a slight increase in acetaldehyde quantity. Adding or decreasing water to the blood had no effect on acetaldehyde. Salting the blood with sodium chloride decreased the yield of acetaldehyde. Adding potassium carbonate produced marked increases in acetaldehyde peaks. Thus, heating the sample to higher temperatures for longer amounts of time and the addition of potassium carbonate increased the quantity of acetaldehyde present in the head space. The sample preparation procedures differentially affected the yield of blood volatile compounds. The analysis of humoral fluid volatile compounds in other species will likely benefit from optimizing sample handling procedures.

To collect sufficient quantity of acetaldehyde for mass spectral identification, potassium carbonate ($K_2CO_3$) was added to the blood and the blood was heated for 30 minutes at 90° C., as described above. Blood head-space gas was derivatized with 2,4-dinitrophenyl hydrazine (DNPH) according to the following procedures.

Frozen cow's blood (250 ml) was thawed in a water bath and 10 ml of the blood added to twelve 30 ml glass vials. The vials were capped and placed in a −60° C. freezer for at least 1 h. The vial caps were removed and 8 g of $K_2CO_3$ was added to each frozen sample. The vials were recapped and refrozen.

Ten mg DNPH was placed in a 0.3 ml glass micro-reaction vial with a rubber septum screw-top lid and dissolved in glacial acetic acid. The vial was then placed in an ice-water slurry, and the slurry and vial placed in a −60° C. freezer for at least 1 h. Three of the 30 ml vials containing bulk blood were removed from the freezer and allowed to thaw at room temperature for 15 minutes, shaken by hand to mix the $K_2CO_3$ and blood, then placed in a 90° C. water bath for 30 minutes.

The micro-reaction vial was removed from the freezer and a 22 gauge needle pierced through the septum to allow a vent for excess pressure. A blood sample was removed from the water bath and 5 ml of head space sampled from it with a Hamilton Gas-Tight syringe, equipped with the Thermo-Syringe (Reno, Nev.) set to 50° C. and a 22 gauge, 1 inch needle. The syringe's needle was then pierced through the septum on the micro-reaction vial and down far enough into the reaction mixture that the end of the needle entered into the excess sediment of DNPH on the bottom of the vial.

The syringe was then put into a Sage Instruments (Cambridge, Mass.) syringe pump. The pump was operated at 2.3 ml min$^{-1}$, and all the head-space sample bubbled through the reaction mixture. Head space was sampled and injected into the DNPH three times from each of the three vials, and then the micro-reaction vial was put back into the freezer, and three more 30 ml vials of blood removed from the freezer for thawing. After the final three 30 ml vials had been sampled, the micro-reaction vial was put back in the freezer for 30 minutes. It was then removed and allow to thaw enough so that it could be removed from the ice around it, and then was allowed to warm to room temperature.

The reaction mixture was pulled into a 5 ml disposable syringe and pushed back through a 0.2 µm disposable syringe filter, with the liquid part of the reaction mixture being collected. Two to three drops of either acetone or hexanal were added to the liquid, and the mixture sonicated for 5 minutes to react with whatever unreacted DNPH may have been present. Hexanal was used because it permitted a more rapid reaction with DNPH. The derivatives with DNPH, however, took too long to elute from the HPLC column, which was used to separate the derivatives. Acetone was therefore used in HPLC runs, and the derivatized peaks collected as separate fractions. An acetaldehyde-free control sample was processed with the acetone procedure, which verified the absence of measurable acetaldehyde contamination of the acetone.

Gas chromatography/mass spectrometry (GC/MS) analysis was performed on a Hewlett-Packard Model 5970 GC/quadruple mass spectrometer coupled to an HP model 5890 GC fitted with an HP Ultra-1 cross-linked methyl silicone microbore capillary column (12.5 m, 0.30 mm O.D., 0.20 mm I.D.). Mass spectral detector (MSD) ionization was by electron impact at 70 eV, ion source (chamber) temperature was 220°–250° C. The MSD was tuned (m/e 69, 219 and 502) with perfluorotri-n-butylamine (PFTBA), normalized to decafluorotriphenylphosphine (DFTPP). The GC transfer line was held at 280° C. The GC was equipped with an on-column injection system.

On-column injection was performed with a 10 µl Hamilton syringe fitted with a 10 cm fused silica needle (O.D. 0.17 mm). The system was controlled by a HP Model 59970A work station. Conditions for on-column injection and GC analysis were as follows: helium (head) pressure 5.5 psi; detector 280° C.; initial column temperature held at 40° C. for 1 minute, followed by ramping at 25° C. min$^{-1}$ to a final temperature of 270° C. These conditions allowed clear separation of DNP derivatives of acetone and acetaldehyde. To verify the effectiveness of derivatization, we used HPLC to show the presence of reacted products. HPLC conditions included use of a C 18 reversed-phase column with methanol-water as the eluting solvent.

In some cows, there was also an early-eluting fifth peak. Mass spectra of blood head-space that was derivatized with DNPH sample and a comparably prepared acetaldehyde standard were studied. The 224 molecular ion is the sum of the mass of DNP (198) and acetaldehyde (44) minus the mass of water, which is eliminated in the reaction. The complete characteristic chromatographic profile appeared 1–3 days prior to estrus.

Acetaldehyde peaks occurred in larger than normal amounts 1–3 days prior to "standing heat" or day of estrus. Since mating behavior occurs a few hours before ovulation, the estrous specific compounds predict both estrus and ovulation. The methods used with regard to bovines apply to any use in any mammalian species wherein one or more humoral volatiles are used to predict and detect estrus in animals or ovulation in humans. In humans, for example, the methods could be used for developing a "rhythm method" birth control diagnostic. The assay could also be used to improve success rates with artificial insemination and embryo transfer, and with oocyte maturation procedures.

EXAMPLE II

Head-space gas chromatography analysis was performed on 10 ml milk samples following the analytical procedures described in Example I. Milk samples were collected in the morning from four cows beginning 6 to 8 days prior to estrus. The results of head-space gas chromatography analysis to determine the quantity of acetaldehyde in the milk samples were observed.

There was a distinct rise and then fall in acetaldehyde quantities, compared to the baseline quantities, just prior to the day of observed behavioral signs of estrus (Day 0). A succession of progressively increasing acetaldehyde peaks prior to estrus were observed. This pattern was unusual, and was observed in only one animal during one estrous cycle. The greatest increase, then decrease in acetaldehyde in that animal, however, occurred just prior to estrus. Thus, monitoring milk acetaldehyde levels would enable predicting the occurrence of estrus and ovulation.

EXAMPLE III

Known chemical reagent tests may also be used to determine the amount of acetaldehyde or other low molecular weight volatile compounds subject to variation during the reproductive cycle present in breath, body cavity air, humoral fluids, or the air above humoral fluids, from humans and animals. In another embodiment of the invention, air adsorbent tubes are used to trap the low molecular weight volatile compound found in body cavity air from the vaginal (reproductive) cavity of cows. The air adsorption tubes (Supelco ORBO™-25) contained an adsorbent and a packing mesh (Supelpak 20N). The adsorbent, 2-(hydroxymethyl)piperidine, reacts with acetaldehyde to trap the acetaldehyde in the mesh for subsequent ultraviolet spectroscopy analysis. Acetaldehyde reacted with 2-(hydroxymethyl)piperidine is stable and non-volatile, and will absorb ultraviolet light at different wavelengths than when unreacted; thus the quantity of acetaldehyde can be measured. Other commercially available air adsorption tubes which may be used to collect the samples include NAPH 226119 (SKC) and NAPH 22627 (SKC). Acetaldehyde adsorption tubes containing DNPH or 1,3-cyclohexanedione are also available for collecting samples containing acetaldehyde.

Vaginal air samples were collected from cows, beginning at approximately day 15 or 16 of the 21 d estrous cycle. In the preferred embodiment, samples were taken at 12 h intervals. In an alternate method, samples may be taken at 24 h intervals. Samples may be taken more frequently, if desired, to monitor the variations in the quantity of the low molecular weight compound present in the sample.

Vaginal air samples were collected by removing the glass seals from an air adsorbent tube and fitting both ends of the tube with a flexible hose. The free end of one of the flexible hoses was then connected to a portable pump having a flow meter calibrated to draw in 500 cc/min of air, for a total collection of a 5 l sample. A 5 l air sample was found to provide sufficient quantities of low molecular weight volatile compound for analysis.

The free end of the second flexible hose was positioned near the vulva but outside of the vaginal cavity of the animal. Because of the volatile nature of acetaldehyde, air collected from outside of the animal's vaginal cavity contained sufficient quantities of acetaldehyde for measuring. The low molecular weight compound collected will be from the reproductive tract air and the vulval gland secretions. Secretions from all skin glands would contain some quantity of acetaldehyde, however, since all body fluid compartments are in equilibrium.

Once the air sample was drawn through the air adsorption tube, the tube was sealed at each end by removing the flexible hoses and capping each end of the tube. The tubes containing the collected sample are frozen in vapor nitrogen or according to recommended procedures for the handling of the air adsorbent tube. The quantity of low molecular weight compound was analyzed using standard ultraviolet spectroscopy techniques.

Graphs of the quantity of acetaldehyde in vaginal air samples obtained from three cows: Cow #1, Cow #2 and Cow #3, respectively, were made. Sampling began during the proestrus phase of each animal's estrous cycle. Samples were taken every 24 h from cow #1, at 12 h intervals from cow #2, and at alternating 1 time/d and twice/d from cow #3 during the collection period to monitor the quantity of acetaldehyde present in the vaginal air. The sample size was five 1 of vaginal air, collected at 500 cc/min. Each sample was collected from outside the body of the animal at the vulvar area, as described herein.

Vaginal air acetaldehyde peaks are shown to vary greatly with day of sampling. However, the peak acetaldehyde quantity followed by a rapid and sharp decline in acetaldehyde in vaginal air consistently occurred at or near estrus. Estrus in all three cows was confirmed by visual observations of standing mating behavior and metestrous bleeding 3–4 days after the drop in acetaldehyde.

The significant quantities of acetaldehyde in vaginal air is correlated with the stages of the estrous cycle. Observations of acetaldehyde spikes in vaginal air will allow the prediction of estrus and/or ovulation in animals and humans.

Since there are extremely dramatic variations in the amount of individual volatile compounds present in body constituents, any technique for measuring the quantity of the compound present, used at spaced apart intervals throughout the cycle will produce an indication of the quantity of the compound present at the time of sampling.

In the alternative, body cavity air samples may be obtained from within the body cavity. For example, the free end of the a tube connected to the air adsorption tube described above may be inserted into the vagina or cervix of a cow and an air sample drawn through the tube. Although this method may be used to obtain samples for monitoring the variations in the quantity of low molecular weight compound in the body cavity air, it is not as desirable from the standpoint that it will require more handling of the animal, resulting in greater stress on the animal. The collection of the sample will also have to be done more slowly so as not to risk collapsing the body cavity as the sample is drawn.

In yet another embodiment of the invention, body cavity air, particularly vaginal (reproductive) cavity air, may be collected using a kit. An air adsorption tube of the type described above in this example is positioned in a cannula. The cannula may be made from any substance, such as plastics, which will not irritate the animal. The wall of the cannula may be of any thickness which will not irritate the animal and must have an internal diameter suitable to accommodate the air adsorption tube. Preferred dimensions for the cannula are 20 cm in length and 2 cm outer diameter with a 2 mm thick wall. A first end of the cannula will have a plurality of holes. A second end of the cannula will be sealed at lid. A first tubing will be connected to air adsorption tube, and exit lid through a first orifice. Tubing is connected to a metered hand held pump. Tubing may be a tygon tubing or other suitable tubing for connecting the air adsorption tube to the pump. A second tubing is connected to pump and enters the cannula through second orifice in lid. The cannula containing the air adsorption tube is placed approximately 10 cm into the vagina of the animal. Activation of the pump draws body cavity air from the body cavity through holes into the cannula and through air adsorption tube. Once the air is drawn through the air adsorption tube, it passes through tubing, through pump and then forced through tubing back into the cannula. The flow of air back into the cannula will facilitate the movement of air into the cannula at holes. Body cavity air samples should be taken slowly so as not to rapidly evacuate the air and collapse the cavity. Drawing 500 cc/min air for a total sample of 5 l of cavity air is preferred. However, less sample may be collected to monitor acetaldehyde quantities present since body cavity air samples taken from inside the animal will not be influenced by barn or environment air, as with samples drawn from outside the animal.

EXAMPLE IV

Humoral fluid samples may also be analyzed using batch mode analyses, wherein a reagent which reacts with the low molecular weight compound subject to variation during the reproductive cycle being measured is added to a humoral fluid sample. The sample is then processed to purify and quantify the reactant using standard spectroscopic or fluorometric techniques.

Acetaldehyde quantities in milk samples collected during the estrous cycle of cows have been measured and monitored to determine the phase of the mammal's reproductive cycle and to predict ovulation and estrus. Quantities of acetaldehyde in the samples were measured using the following described procedures.

A 25 ml milk sample is collected and 2 ml saturated sodium chloride (NaCl) and 20 ml hexane added. The milk, NaCl and hexane mixture is shaken and allowed to stand for 5 min. The hexane layer separates and will contain milk lipids. The top layer of hexane and lipids is pipetted off and discarded. Proteins are precipitated from the remaining sample by adding 7 ml of 3M potassium carbonate ($K_2CO_3$) and centrifuging 5 min at 2000 g. The supernatant is removed and 2.5 ml DNPH solution (1 mg/ml DNPH in 6M HCl) added. The sample is then heated on a shaker at 60° C. for 10 min for the reaction to occur. The sample is filtered using standard filter paper and 2 ml of filtrate slowly loaded into a C18 solid-phase extraction cartridge. The C18 cartridge is rinsed 1 min with water, followed by 1 min with dilute acid (1% HCl). The DNPH-acetaldehyde reactant diluted with 2 ml acetonitrile. This step takes approximately 3 min. A 20 µl sample of the DNPH-acetaldehyde eluate is injected into an HPLC and read at UV wavelength 360.

In alternate methods, 7 ml of 3M perchloric acid may be added instead of 7 ml $K_2CO_3$ to precipitate proteins. As another alternative, 1,3-cyclohexanedione solution may be added instead of DNPH solution. Other batch mode analyses of samples for quantifying the quantity of acetaldehyde in a humoral fluid sample will be known to those skilled in the art.

Batch processing milk and other humoral fluid samples to monitor variations in the quantity of acetaldehyde or other low molecular weight volatile compound subject to variation during the reproductive cycle can easily be used to monitor reproductive cycles in humans and animals.

EXAMPLE V

Air collected from above a humoral fluid may be analyzed to measure the quantity of a low molecular weight volatile compound subject to variation during the reproductive cycle. A kit for sampling the air above humoral fluids, such as milk and blood, may be used to monitor cycles. A humoral fluid sample is placed in a container, which is then placed in a sonication bath. An air pump is used to force air through tubing and into the sample, thereby increasing the amount of low molecular weight volatile compound moving out of the humoral fluid. The sonication bath further facilitates flushing the low molecular weight volatile compound out of the humoral fluid and into the air above the fluid. It is preferred that the container be sealed with a lid, with tubing and an entry tube passing through lid at a first orifice and a second orifice, respectively. Sealing the container will reduce the escape of the low molecular weight volatile compound.

The air above the humoral fluid is drawn into entry tube and through an air adsorption tube by pump. The low molecular weight volatile compound present in the air above the humoral fluid will be trapped in the air adsorption tube. The air adsorption tube may be any of the types described in Example III herein. Exit tube connects the air adsorption tube to the pump. The flow of air from the pump follows the path described into the humoral fluid and back into the pump follows the path described.

It is preferred that a 5 l sample of air above the humoral fluid be taken. The low molecular weight volatile compound trapped in the air adsorption tube may be analyzed using the procedures described in Example III herein. A larger or smaller volume may be taken, however, if adequate for quantifying the low molecular weight volatile compound using analytical techniques known to those in the art.

EXAMPLE VI

Low molecular weight volatile compounds subject to variation during the reproductive cycle may be measured by commercially available electrochemical detectors. An electrochemical detector capable of detecting and measuring a selected low molecular weight volatile compound, such as acetaldehyde, can be attached to the tail area of a cow. The electrochemical detector will measure the quantity of the low molecular weight volatile compound in the air above skin gland secretions in the area of the vulva as well as air emitting form the reproductive cavity or vagina. The detector may be designed to have an audio or visual means for signalling a change, or alerting a herdsman that the quantities of acetaldehyde, or other low molecular weight volatile compound present in body cavity air and/or in air above skin gland secretions has reached a particular level indicative of the peak observed near the time of estrus and/or ovulation.

EXAMPLE VII

Low molecular weight volatile compounds subject to variation during the reproductive cycle may also be monitored by measuring the quantity of the compound in a sample obtained from the mouth of a mammal. This method would be preferred for use in predicting ovulation in humans. An oral collection pad may be used to collect a sample of oral fluid with increased concentrations of serum analytes. The swab would then be analyzed to determine the quantity of low molecular weight volatile compound, such as acetaldehyde, in the sample. Samples would be taken a multiple number of times, beginning prior to ovulation, in order to monitor the variations in the quantity of compound present in each sample. A sharp increase in acetaldehyde, or other compound being monitored, followed by a sharp decline in the amount of the compound, will enable predicting the occurrence of ovulation.

The examples included are not intended to limit the scope of the present invention. Other substitutions, modifications and variations are apparent to those skilled in the art without departing from the disclosure and scope of the invention.

What is claimed is:

1. A method for monitoring mammalian reproductive cycles, comprising the steps of:
    (a) collecting a sample of a body constituent selected from the group consisting essentially of humoral fluid, breath and body cavity air from a female mammal;
    (b) measuring the quantity of a low molecular weight volatile compound subject to variation during the reproductive cycle in the sample;
    (c) repeating steps (a) and (b) over a predetermined period of time during the female mammal's reproductive cycle; and
    (d) monitoring variations in the quantity of the low molecular weigh volatile compound measured to determine the phase of the mammal's reproductive cycle and to predict ovulation.

2. The method for monitoring mammalian reproductive cycles of claim 1, wherein the humoral fluid is selected from the group consisting essentially of blood, vaginal secretions, saliva, urine, milk, sweat, skin gland secretions, follicular fluid and air above the humoral fluid.

3. The method for monitoring mammalian reproductive cycles of claim 1, wherein the low molecular weight volatile compound has a molecular weight of less than 50 grams per mole.

4. The method for monitoring mammalian reproductive cycles of claim 1, wherein the low molecular weight volatile compound is acetaldehyde.

5. The method for monitoring mammalian reproductive cycles of claim 1, wherein step (a) further comprises separating the body constituent sample into a nonvolatile compounds fraction and a volatile compounds fraction.

6. The method for monitoring mammalian reproductive cycles of claim 1, wherein the breath and body cavity air samples are collected from outside of the mammal's body.

7. The method for monitoring mammalian reproductive cycles of claim 1, wherein the quantity of the low molecular weight volatile compound is measured by head-space gas chromatography.

8. The method for monitoring mammalian reproductive cycles of claim 1, wherein the quantity of the low molecular weight volatile compound is measured using a chemical reagent test.

9. The method for monitoring mammalian reproductive cycles of claim 1, wherein the quantity of the low molecular weight volatile compound is measured using an electrochemical detector.

10. The method for monitoring mammalian reproductive cycles of claim 1, wherein the quantity of the low molecular weight volatile compound is measured using a biochemical reagent test.

11. The method for monitoring mammalian reproductive cycles of claim 1, wherein the quantity of the low molecular weight volatile compound is measured using immunochemical methods.

12. The method for monitoring mammalian reproductive cycles of claim 1, wherein the quantity of the low molecular weight volatile compound is measured using photochemical methods.

13. The method for monitoring mammalian reproductive cycles of claim 1, wherein the mammal is a primate and the quantity of the low molecular weight volatile compound in the sample of body constituent increases as compared to baseline several days prior to baseline and then subsequently decreases to approximately baseline within approximately 24 hours of ovulation, whereby the approximate time of ovulation can be predicted.

14. The method for monitoring mammalian reproductive cycles of claim 1, wherein the mammal is a nonprimate and the quantity of the low molecular weight volatile compound in the sample of body constituent increases as compared to baseline and then subsequently decreases to approximately baseline at approximately estrus.

15. The method for monitoring mammalian reproductive cycles of claim 1, wherein the quantity of more than one low molecular weight volatile compound is measured.

16. A method for predicting estrus and ovulation in animals, comprising the steps of:
(a) collecting a sample of a body constituent selected from the group consisting essentially of humoral fluid, breath, and body cavity air from an animal a preselected number of times during proestrus;
(b) measuring the quantity of a low molecular weight volatile compound subject to variation during the reproductive cycle in the samples collected; and
(c) monitoring variations in the quantity of the low molecular weight volatile compound in the samples collected to predict the onset of estrus and ovulation.

17. The method for predicting estrus and ovulation in animals of claim 16, wherein the quantity of the low molecular weight volatile compound increases as compared to baseline and then subsequently decreases to approximately baseline at approximately the onset of estrus, whereby the occurrence of ovulation can be predicted.

18. The method for predicting estrus and ovulation in animals of claim 16, wherein the humoral fluid is selected from the group consisting essentially of blood, vaginal secretions, saliva, urine, milk, sweat, skin gland secretions, follicular fluid, and air above the humoral fluid.

19. The method for predicting estrus and ovulation in animals of claim 16, wherein the low molecular weight volatile compound has a molecular weight of less than 50 grams per mole.

20. The method for predicting estrus and ovulation in animals of claim 16, wherein the low molecular weight volatile compound is acetaldehyde.

21. The method for predicting estrus and ovulation in animals of claim 16, wherein step (a) further comprises separating the sample of body constituent into a nonvolatile compounds fraction and a volatile compounds fraction.

22. The method for predicting estrus and ovulation in animals of claim 16, wherein the breath and body cavity air samples are collected from outside of the animal's body.

23. The method for predicting estrus and ovulation in animals of claim 16, wherein the quantity of the low molecular weight volatile compound is measured by headspace gas chromatography.

24. The method for predicting estrus and ovulation in animals of claim 16, wherein the quantity of the low molecular weight volatile compound is measured using a chemical reagent test.

25. The method for predicting estrus and ovulation in animals of claim 16, wherein the quantity of the low molecular weight volatile compound is measured using an electrochemical detector.

26. The method for predicting estrus and ovulation in animals of claim 16, wherein the quantity of more than one low molecular weight volatile compound is measured.

27. A method for predicting estrus and ovulation in animals in the field, comprising the steps of:
(a) monitoring variations in the quantity of a low molecular weight compound subject to variation during the reproductive cycle in a sample of a body constituent selected from the group consisting essentially of humoral fluid, breath, and body cavity air of an animal during the reproductive cycle; and
(b) predicting estrus and ovulation in the animal based on the variations in the quantity of the low molecular weight volatile compound present in the body constituent selected.

28. The method for predicting estrus and ovulation in animals in the field of claim 27, wherein the humoral fluid is selected from the group consisting essentially of blood, vaginal secretions, saliva, urine, milk, sweat, vulval skin gland secretions, follicular fluid, and air above the humoral fluid.

29. The method for predicting estrus and ovulation in animals in the field of claim 27, wherein the low molecular weight volatile compound has a molecular weight of less than 50 grams per mole.

30. The method for predicting estrus and ovulation in animals in the field of claim 27, wherein the low molecular weight volatile compound is acetaldehyde.

31. The method for predicting estrus and ovulation in animals in the field of claim 27, wherein the body cavity air sample is collected from outside of the animal's body near the vulva.

32. The method for predicting estrus and ovulation in animals in the field of claim 27, wherein the variations in the low molecular weight volatile compound are monitored using a chemical reagent test.

33. The method for predicting estrus and ovulation in animals in the field of claim 27, wherein more than one low molecular weight volatile compound is monitored.

34. The method for predicting estrus and ovulation in animals in the field of claim 27, wherein the quantity of the low molecular weight volatile compound in the sample of body constituent increases several days prior to baseline as compared to baseline and then subsequently decreases to approximately baseline within approximately 24 hours of ovulation, whereby the approximate time of ovulation can be predicted.

35. The method for predicting estrus and ovulation in animals in the field of claim 27, wherein the quantity of the low molecular weight volatile compound in the sample of body constituent increases as compared to baseline and then subsequently decreases to approximately baseline at approximately estrus.

* * * * *